(12) United States Patent
Millar

(10) Patent No.: US 11,826,210 B2
(45) Date of Patent: Nov. 28, 2023

(54) MULTIPURPOSE HOLDING SYSTEM FOR PERFUSION ACCESSORIES

(71) Applicant: Allen Currie Millar, Rogers, AR (US)

(72) Inventor: Allen Currie Millar, Rogers, AR (US)

(*) Notice: Subject to any disclaimer, the term of this patent is extended or adjusted under 35 U.S.C. 154(b) by 0 days.

(21) Appl. No.: 17/723,710

(22) Filed: Apr. 19, 2022

(65) Prior Publication Data

US 2023/0329835 A1    Oct. 19, 2023

(51) Int. Cl.
    *H02G 3/04*       (2006.01)
    *A61B 90/57*      (2016.01)
    *F16M 13/02*      (2006.01)

(52) U.S. Cl.
    CPC ........... *A61B 90/57* (2016.02); *F16M 13/022* (2013.01)

(58) Field of Classification Search
    CPC .............................. A61B 90/57; F16M 13/022
    See application file for complete search history.

(56) References Cited

U.S. PATENT DOCUMENTS

| | | | |
|---|---|---|---|
| 3,894,706 A | 7/1975 | Mizusawa | |
| 4,702,448 A | 10/1987 | LoJacono | |
| 4,953,819 A | 9/1990 | Davis | |
| 5,593,392 A | 1/1997 | Starchevich | |
| 5,681,539 A | 10/1997 | Riley | |
| 6,409,131 B1 | 6/2002 | Bentley et al. | |
| 7,533,854 B2 | 5/2009 | Aube | |
| 8,197,447 B2* | 6/2012 | Wright | A61M 25/02 604/179 |
| D678,533 S | 3/2013 | Bernstein | |
| 10,190,609 B2 | 1/2019 | Turturro et al. | |
| 10,694,986 B2 | 6/2020 | Hoan et al. | |
| 11,095,104 B2* | 8/2021 | Frierson | H02G 3/0431 |
| 11,285,296 B1* | 3/2022 | Benz | A61M 25/0662 |
| 2008/0011907 A1 | 1/2008 | Jacobsma | |
| 2009/0281565 A1* | 11/2009 | McNeese | A61B 17/1325 606/201 |
| 2014/0259557 A1 | 9/2014 | Egan | |

OTHER PUBLICATIONS

PCT/US23/17600—International Search Report—dated Jul. 3, 2023.

* cited by examiner

*Primary Examiner* — Amy J. Sterling
(74) *Attorney, Agent, or Firm* — Dennis D. Brown; Brown Patent Law, P.L.L.C.

(57) ABSTRACT

An apparatus and method which uses a flat or curved clipping base mount and one or more instrument or equipment holders to hold instruments and devices in a treatment area to perform cardiovascular or perfusion procedures.

14 Claims, 18 Drawing Sheets

MULTIPURPOSE HOLDING SYSTEM FOR PERFUSION ACCESSORIES

FIELD OF THE INVENTION

The present invention relates to tools, instruments, and devices used in cardiovascular perfusion systems, procedures, and treatments, and also relates to apparatuses, systems, and methods for holding such tools, instruments, and devices.

BACKGROUND OF THE INVENTION

A cardiovascular surgical procedure or treatment can involve the use of various tools, instruments, and other devices. Examples of such devices include, but are not limited to, pressure transducers, stopcock manifolds which allow multiple infusions to connect to a single recirculation line, hemoconcentrators, tubing clamps, ultrasonic flow probes, temperature probes, etc. A need exists for an improved apparatus, system, and method for holding such devices which (a) reduces clutter in the treatment area, (b) enhances the accessibility of accessory devices, (c) preserves space for additional equipment, (d) safely secures and protects the devices and other equipment, and (e) is easy and inexpensive to install and use.

SUMMARY OF THE INVENTION

The present invention satisfies the needs and alleviates the problems discussed above. In one aspect, there is provided an apparatus for multiple perfusion procedures and accessories comprising a clipping base mount and a perfusion instrument or equipment holder. The clipping base mount preferably comprises a base mount and an opposing pair of clipping brackets on an exterior of the base mount. The opposing pair of clipping brackets preferably comprise a left bracket and a right bracket. The left bracket comprises a left bracket slot which ha open upper end and a closed lower end. The right bracket comprises a right bracket slot which has an open upper end and a closed lower end. The left bracket slot faces the right bracket slot. The left bracket slot, or at least a segment of the left bracket slot, preferably, has a width, between a rearward interior wall and a forward interior wall of the left bracket slot, which decreases as the left bracket slot extends downwardly to the closed lower end of the left bracket slot or to a clipping segment in a bottom end portion of the left bracket slot. The right bracket slot, or at least a segment of the right bracket slot, preferably has a width, between a rearward interior wall and a forward interior wall of the right bracket slot, which decreases as the right bracket slot extends downwardly to the closed lower end of the right bracket slot or to a clipping segment a bottom end portion of the right bracket slot.

The perfusion instrument or equipment holder preferably comprises a holder body and a clipping mount structure, provided on the holder body, which is receivable in the opposing pair of brackets of the clipping base mount. The clipping mount structure of the perfusion instrument or equipment holder preferably comprises (a) a projecting left shoulder plate which slides into the left bracket slot of the left bracket and (b) a projecting right shoulder plate which slides into the right bracket slot of the right bracket.

Further aspects, features and advantages of the present invention will be apparent to those in the art upon examining the accompanying drawings and upon reading the following Detailed Description of the Preferred Embodiments.

DETAILED DESCRIPTION OF THE PREFERRED EMBODIMENTS

Figure 1:
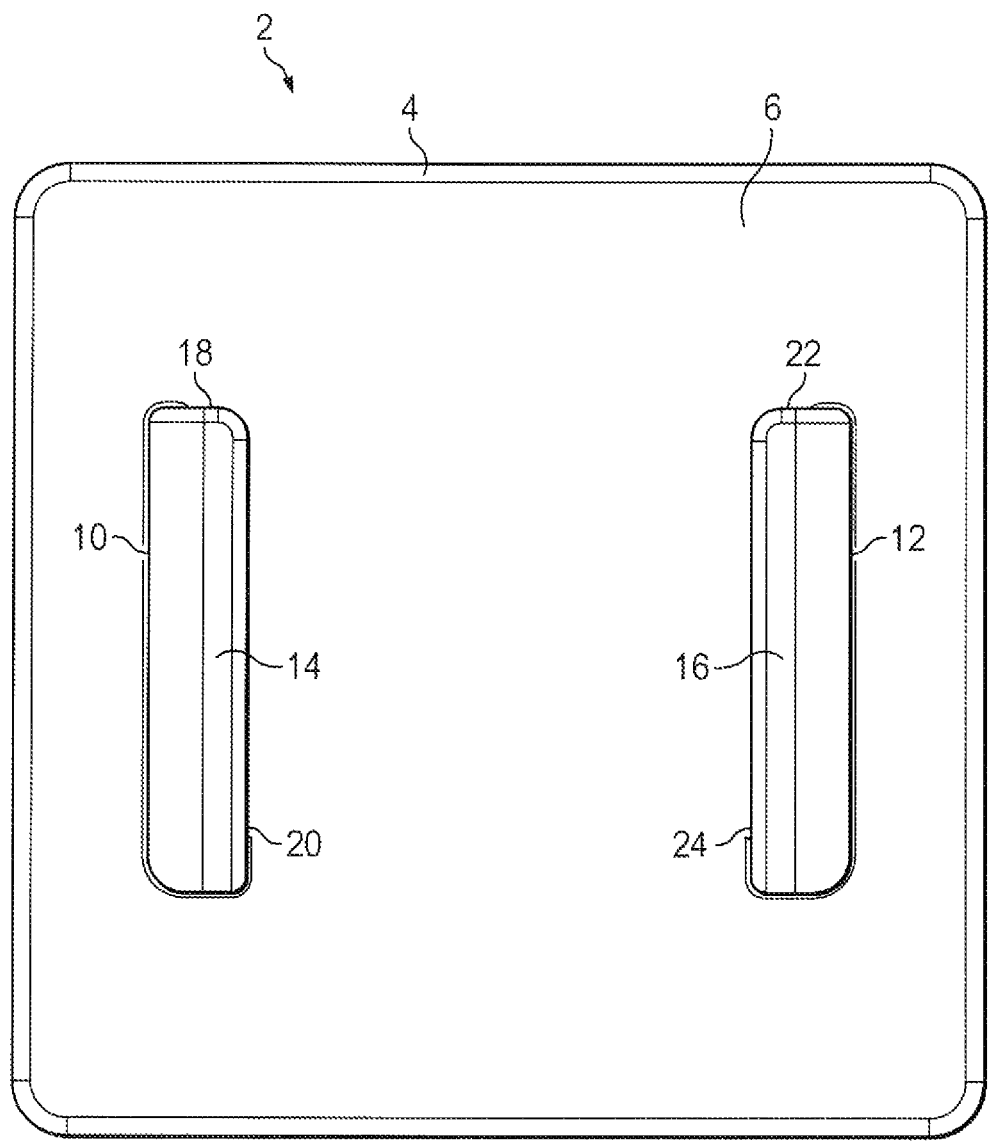
FIG. 1 is an elevational front view of a flat embodiment 2 of a clipping base mount used in the inventive multipurpose holding system.
Figure 2:
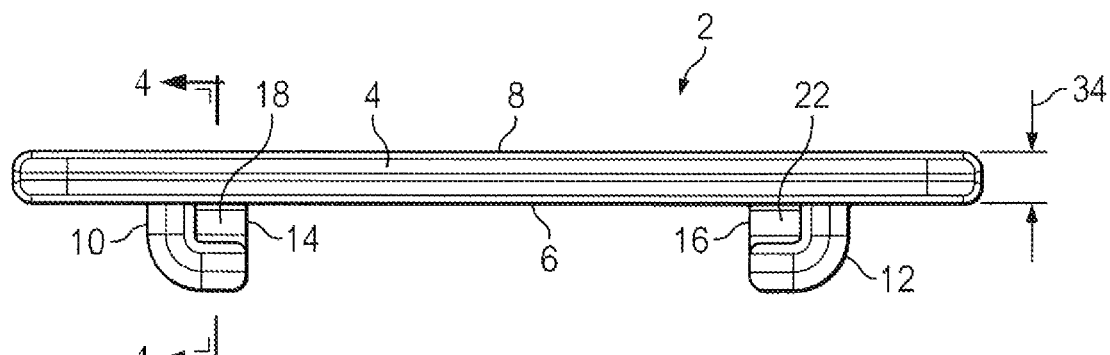
FIG. 2 is a top view of the flat clipping base mount 2.
Figure 3:
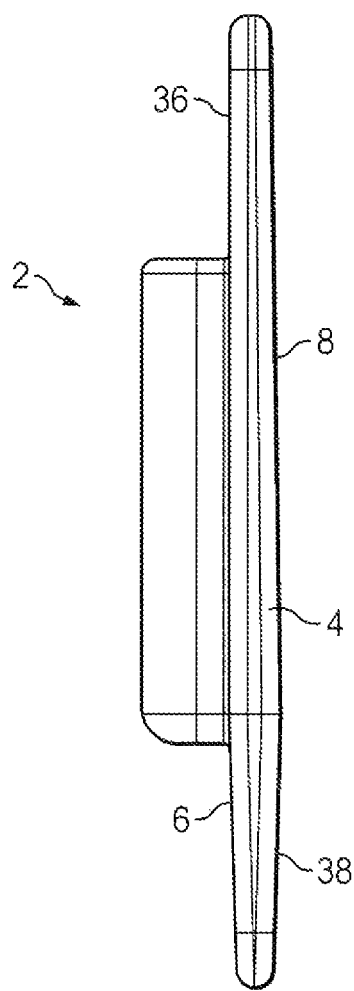
FIG. 3 is an elevational side view of the flat clipping base mount 2.

An embodiment 2 of a clipping base mount used in inventive multipurpose holding apparatus for holding instruments and devices used in perfusion procedures is illustrated in FIGS. 1-5. The clipping base mount 2 preferably comprises: (a) a base panel mount 4 having a front surface 6 and a back surface 8 and (b) an opposing pair of dipping brackets 10 and 12 which project from the front surface 6 of the base panel mount 4.

The bas panel mount 4 of the clipping base mount 2 is flat, or substantially flat and, although other shapes can alternatively be used, is preferably rectangular. By way of example, but not by way of limitation, glue, other adhesives, or a hook and loop attachment can be used on the back surface 8 of the base panel mount 4 to attach the dipping base mount 2 to a flat surface in the perfusion treatment area. Alternatively, mechanical attachments (e.g., screws) could be used to attach the clipping base mount 2 to a flat surface where appropriate. Examples of typical locations in perfusion treatment areas having flat surfaces to which the clipping base mount 2 can be attached include, but are not limited to, the flat sides of individual roller pumps and flat shelf surfaces.

In the dipping base mount 2, the opposing pair of clipping brackets 10 and 12 comprises a vertically extending left bracket 10 and a vertically extending right bracket 12. The vertically extending left bracket 10 has a vertically extending left bracket slot 14 which faces a corresponding, vertically extending right bracket slot 16 provided by the vertically extending right bracket 12. The vertically extending left bracket slot 14 has an open upper end 18 and a closed lower end 20. The vertically extending right bracket slot 16 has an open upper end 22 and a closed lower end 24.

Figure 4:
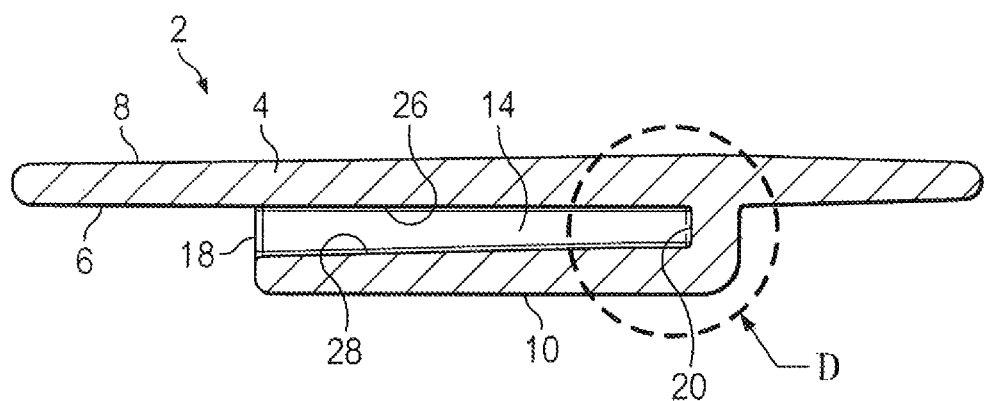
FIG. 4 is a cross-sectional view of the flat clipping base mount 2 as seen from perspective 4-4 shown n FIG. 3.
Figure 5:
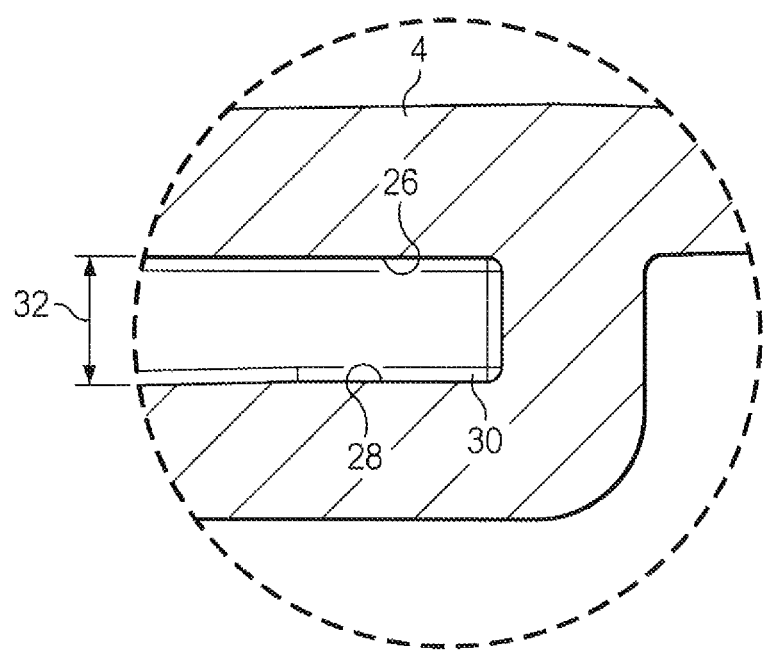
FIG. 5 is an enlarged view of the section of the flat clipping base mount 2 which is circled in FIG. 4.
Figure 6:
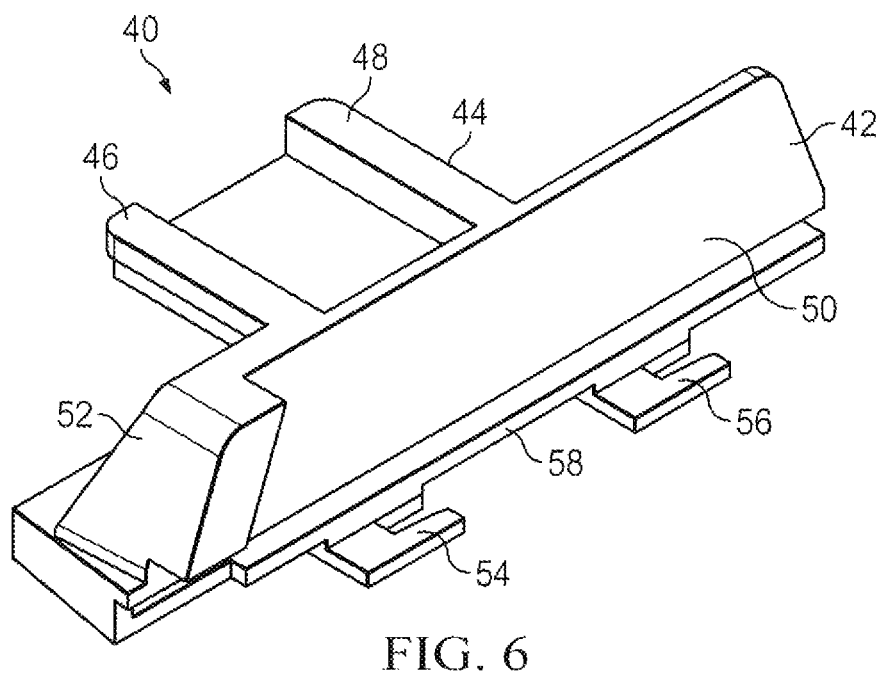
FIG. 6 is a perspective view of an embodiment 40 of a horizontal perfusion instrument or equipment holder used in inventive multipurpose holding apparatus for holding a multiport manifold.
Figure 7:
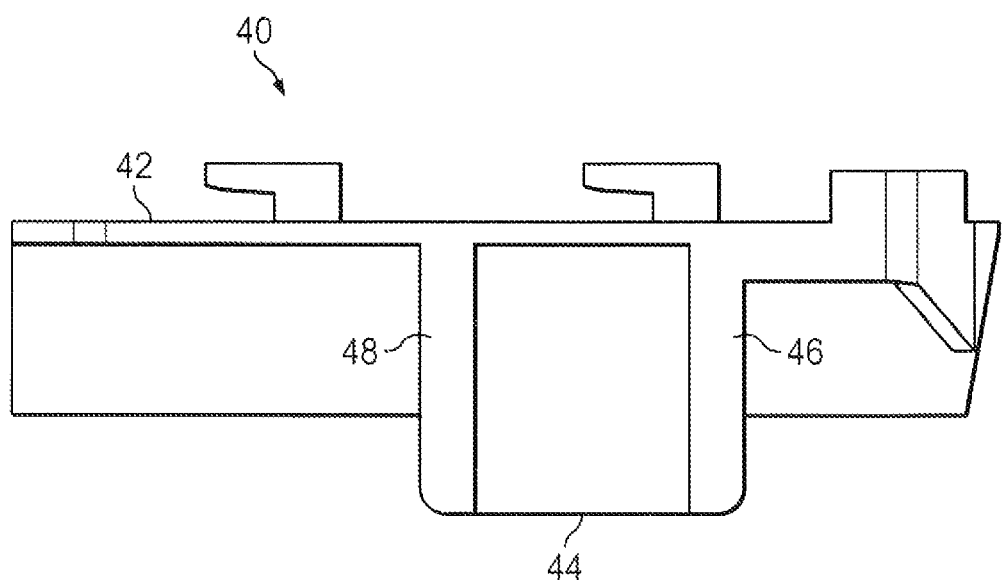
FIG. 7 is an elevational rear view of the manifold holder 40.
Figure 8:
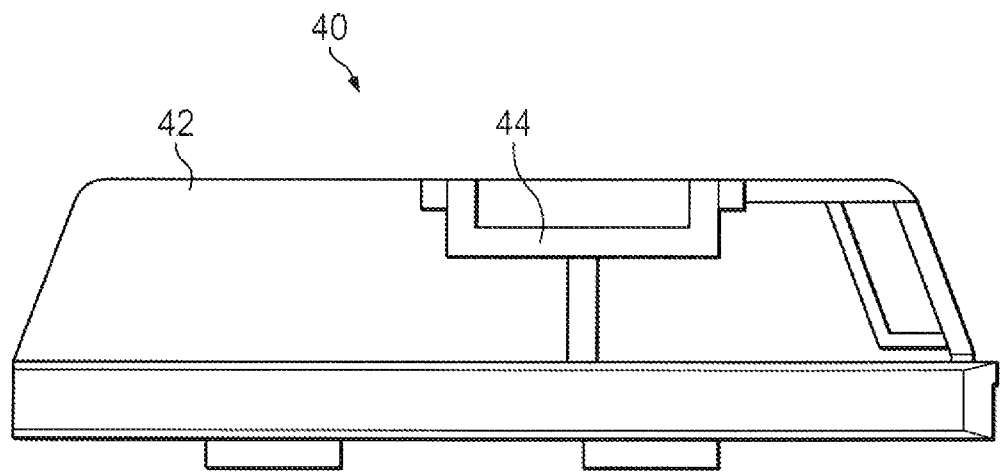
FIG. 8 is a bottom view of the manifold holder 40.
Figure 9:
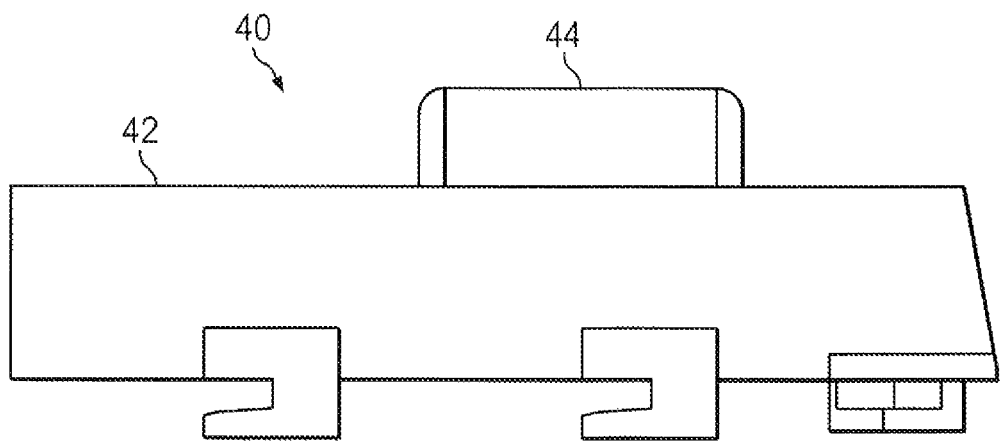
FIG. 9 is an elevational rear view of the manifold holder 40.
Figure 10:
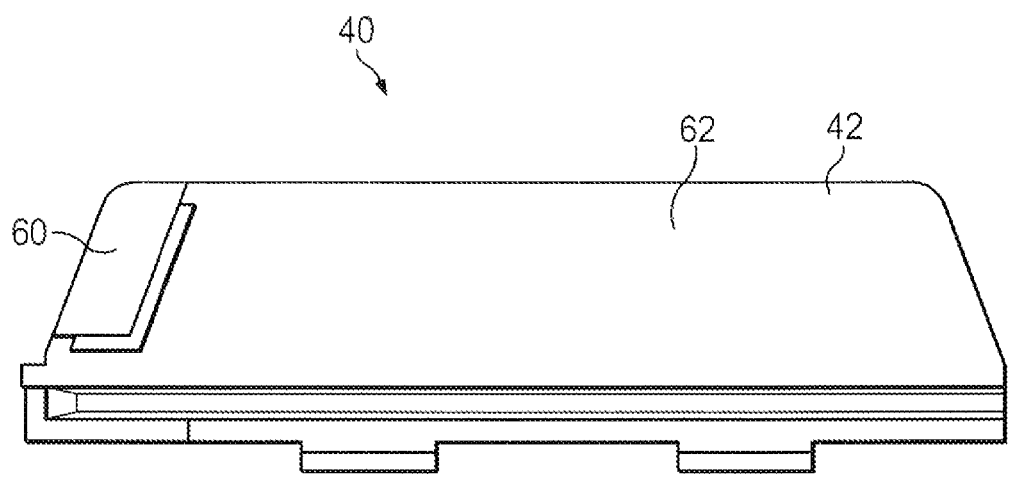
FIG. 10 is a top view of the manifold holder 40.
Figure 11:
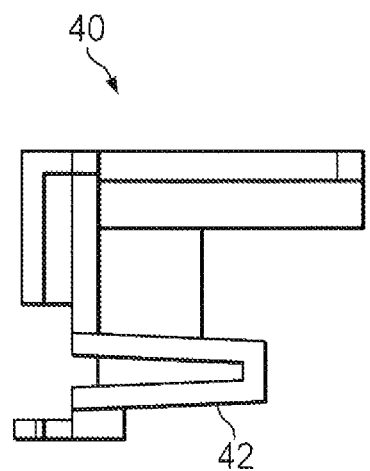
FIG. 11 is a left end view of the manifold holder 40.
Figure 12:
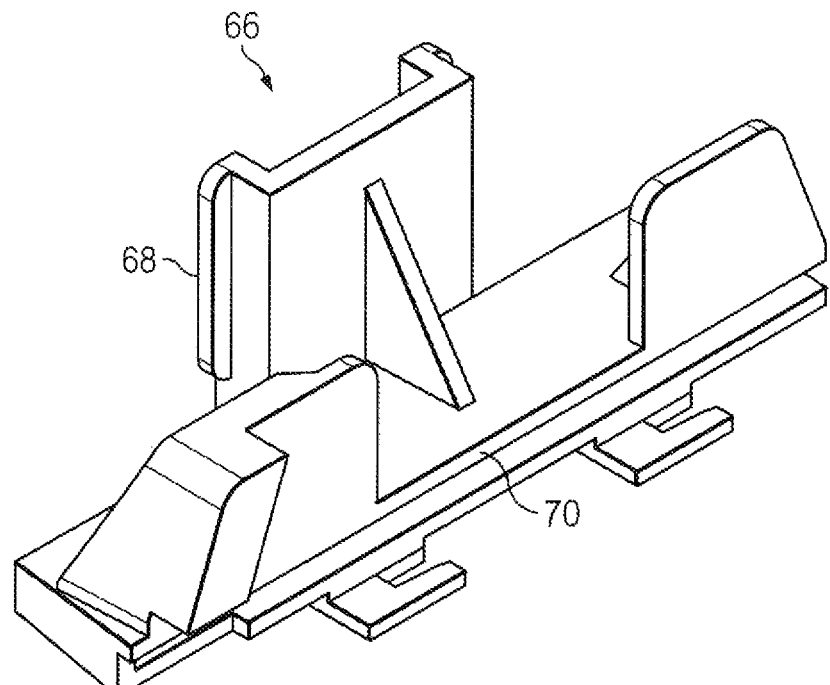
FIG. 12 is a perspective view of an embodiment 66 of a vertical manifold holder which is used in the inventive multipurpose holding apparatus.
Figure 13:
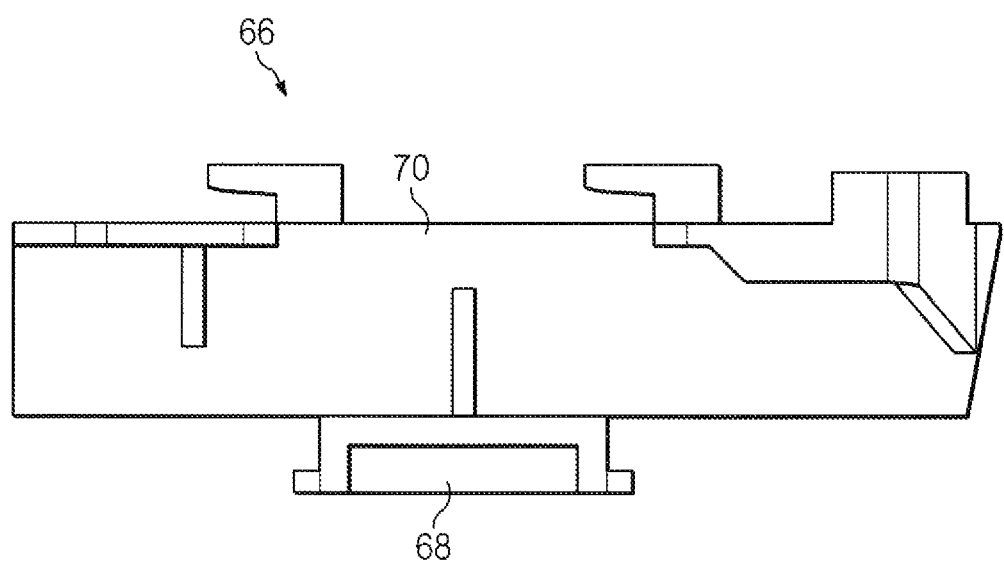
FIG. 13 is a front view of the manifold holder 66.
Figure 14:
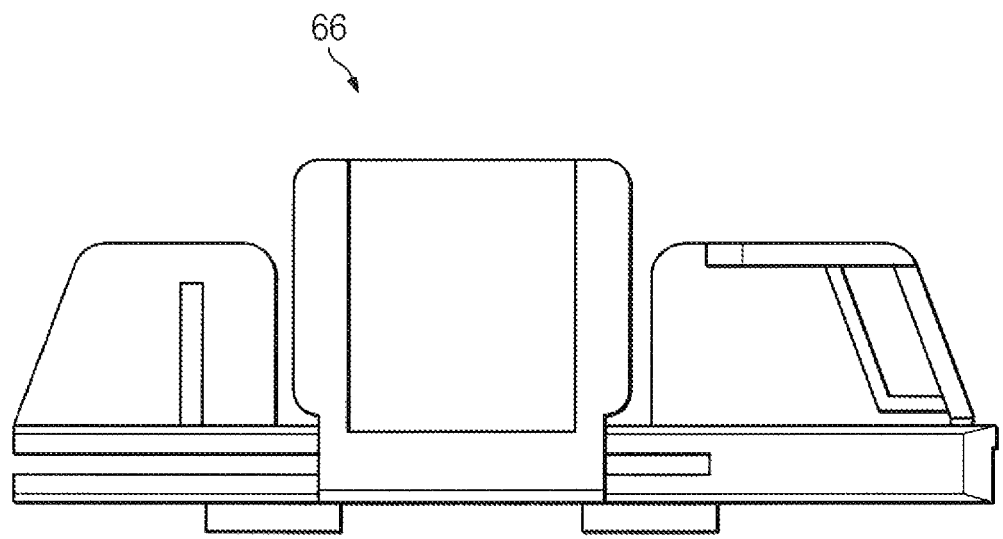
FIG. 14 is an elevational back view of the manifold holder 66.
Figure 15:
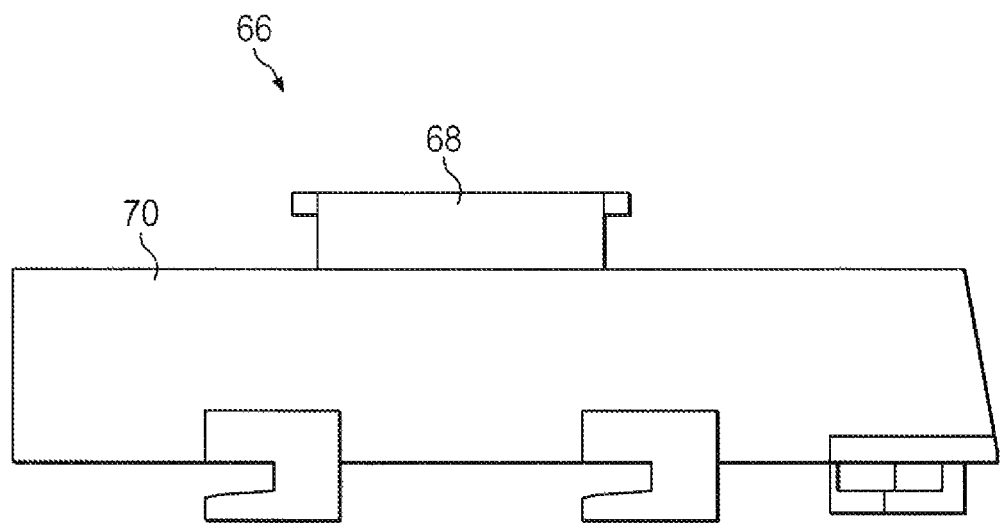
FIG. 15 is a front inverted view of the manifold holder 66.
Figure 16:
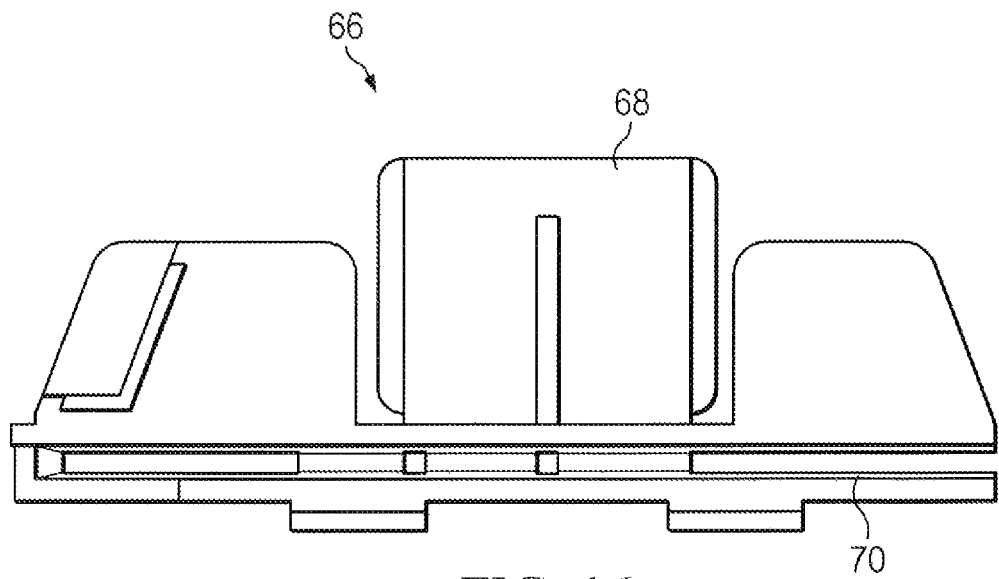
FIG. 16 is a top view of the manifold holder 66.
Figure 17:
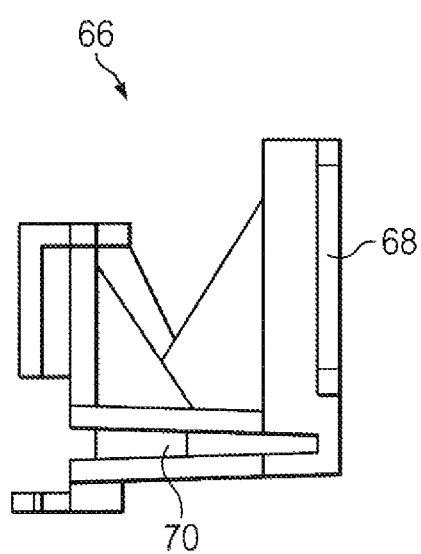
FIG. 17 is a right end view of the manifold holder 66.
Figure 18:
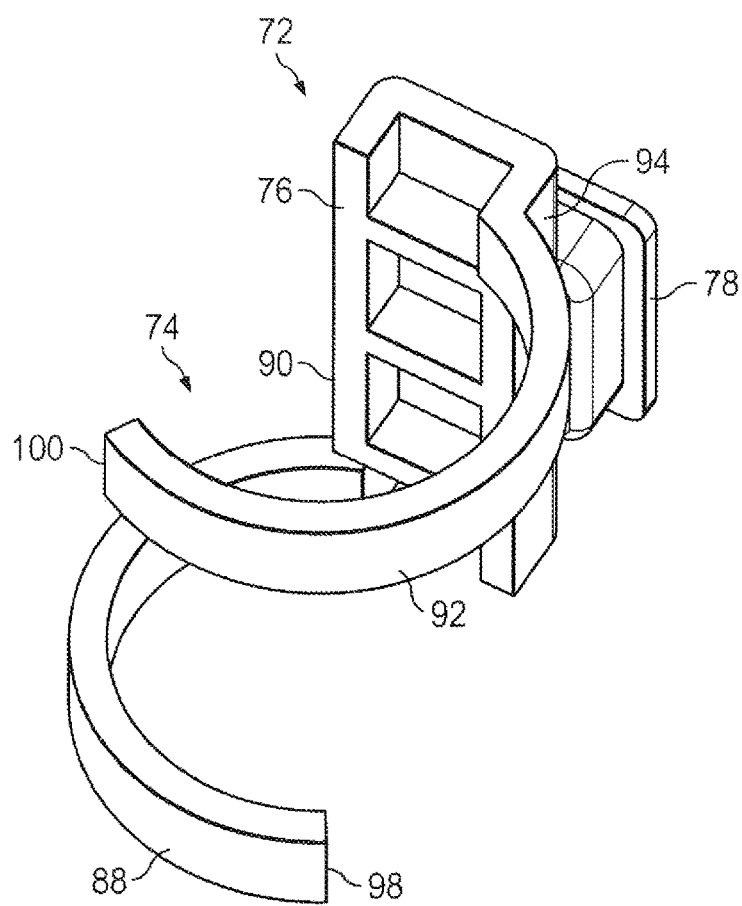
FIG. 18 is a perspective view of an embodiment 72 of a perfusion instrument or equipment holder used in inventive multipurpose holding apparatus for holding a hemoconcentrator in a vertical or horizontal position.
Figure 19:
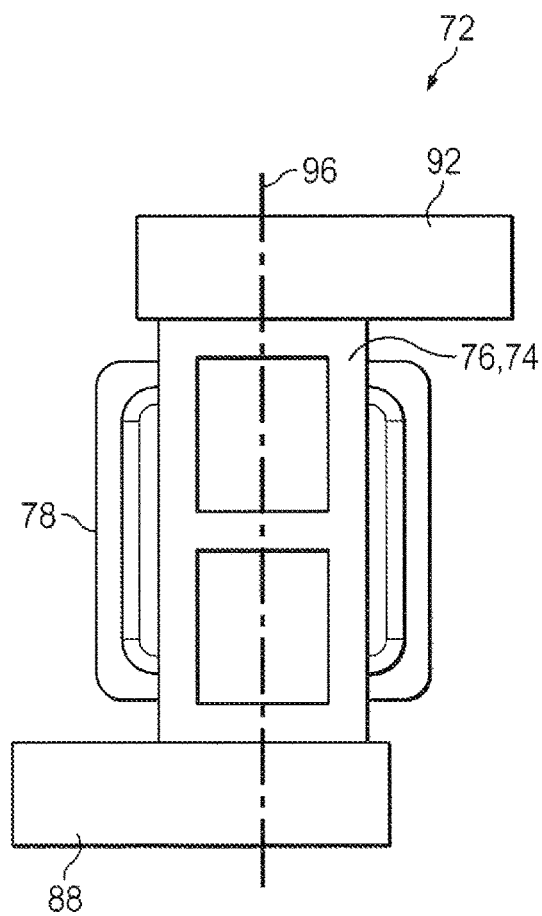
FIG. 19 is a front elevational view of the hemoconcentrator holder 72.
Figure 20:
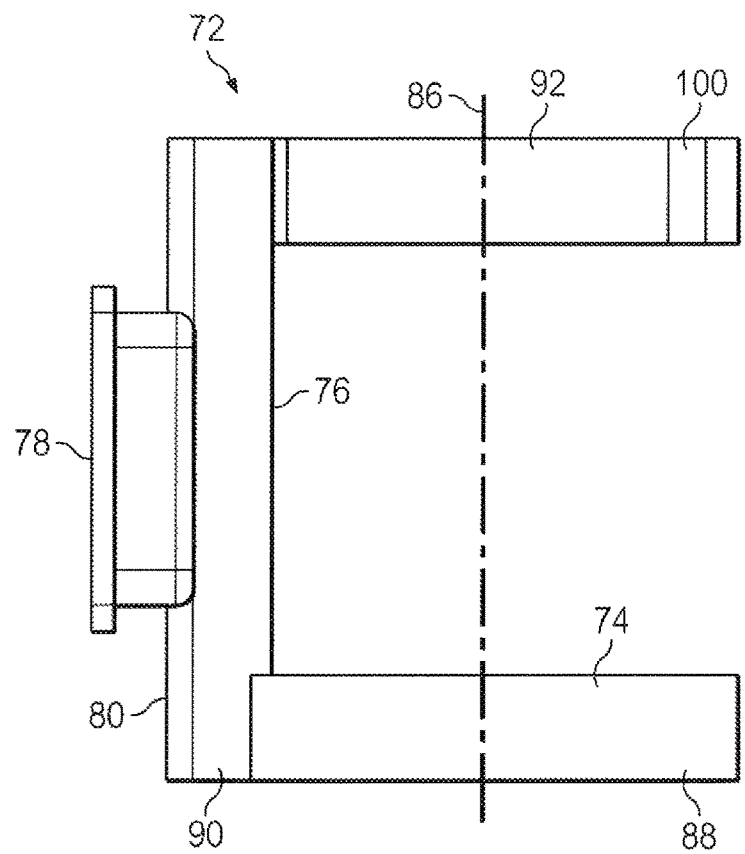
FIG. 20 is a left side elevational view of the hemoconcentrator holder 72.
Figure 21:
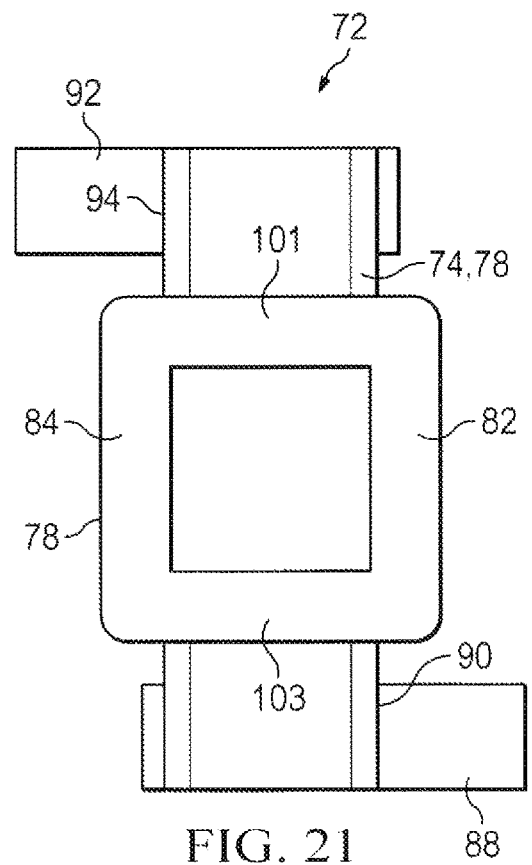
FIG. 21 is a back elevational view of the hemoconcentrator holder 72.
Figure 22:
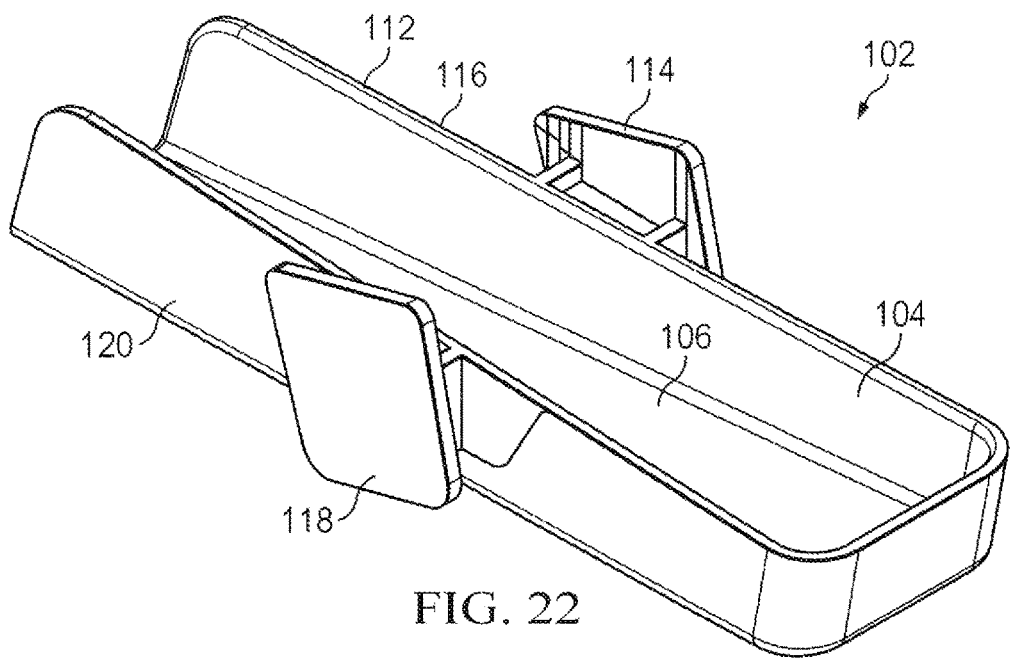
FIG. 22 is perspective view of air embodiment 102 of a perfusion instrument or equipment holder used in the inventive multipurpose holding apparatus wherein the body of the holder 102 is a tube clamp tray 104.
Figure 23:
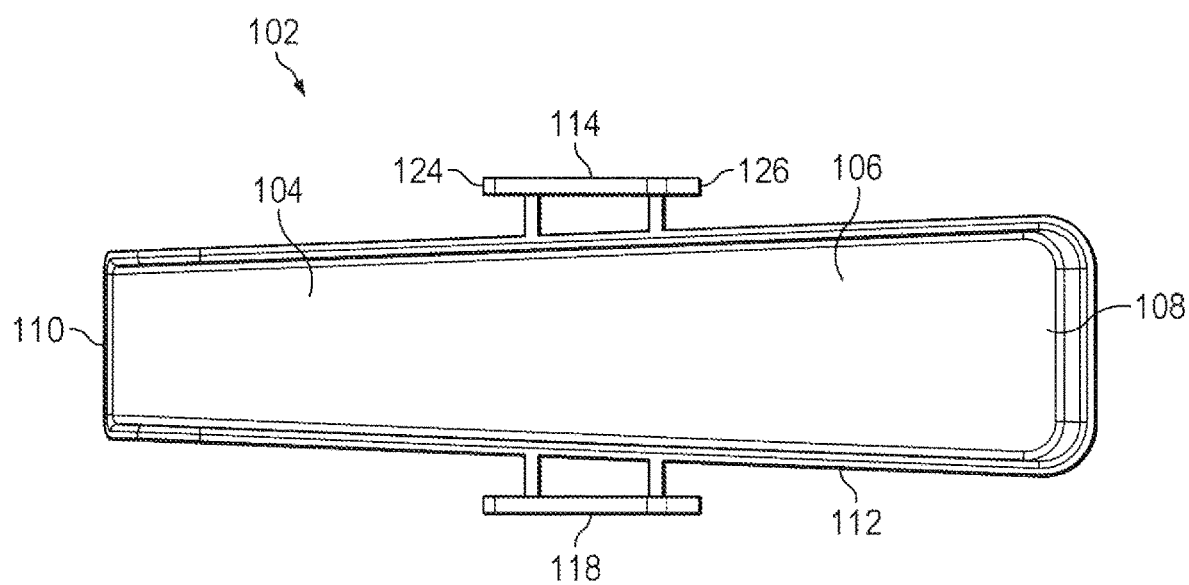
FIG. 23 is a top view of the tube clamp tray holder 102.
Figure 24:
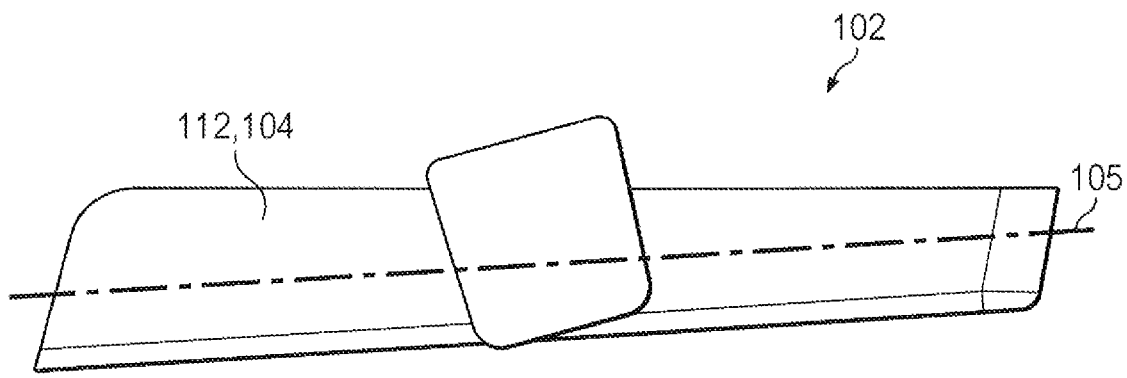
FIG. 24 is an elevational side view of the tube clamp tray holder 102.

As illustrated in FIGS. 4 and 5, each of the vertically extending bracket slots 14 and 16 provided within the vertically extending left and right brackets 10 and 12 of the clipping base mount 2 has a vertically extending rearward interior wall 26 and a vertically extending forward interior wall 28. To assist in clipping any one of the inventive perfusion instrument or equipment holders discussed below in the opposing pair of clipping brackets 10 and 12, the vertically extending forward interior wall 28, or at least a segment, e.g., of the lower half of the wall 28, of each of the bracket slots 14 and 16 will preferably taper rearwardly toward the vertically extending rearward interior wall 26 as the forward interior wall 28 extends downwardly.

As the vertically extending bracket slots 14 and 16 extend downwardly, the inward taper of the vertically extending forward interior wall 28 of each of the vertical slots 14 or 16, or at least a segment, e.g., of the lower half of the wall 28, can continue all of the way to the closed bottom end 20 or 24 of the vertically extending bracket slot 14 or 16 or can continue to a short clipping segment 30 of the vertical slot 14 or 16 at the bottom of the bracket slot 14 or 16. The short clipping segment 30 has a constant cross-sectional size and shape as it extends downwardly and has a height of not more than 20%, more preferably not more than 15% or not more than 10%, of the total height of the vertically extending bracket slot 14 or 16.

Consequently, as the vertically extending bracket slots 14 and 16 extend downwardly, the width 32 of each of the vertically extending left and right bracket slots 14 and 16 between the vertically extending forward interior wall 28 and the vertically extending rearward interior wall 26 thereof decreases, at least in a segment, e.g., in the lower half of the bracket slot 14 or 16. The decrease in the width 32 of the vertically extending bracket slot 14 or 16 can continue all of the way to the closed bottom end 20 or 24 of the vertically extending bracket slot 14 or 16 or can continue to short clipping segment 30, the short clipping segment 30 having a constant width 32 as it extends downwardly.

The base panel mount 4 of the clipping base mount 2 can have a constant or substantially constant thickness 34 throughout. More preferably, an upper portion 36 of the thickness 34 of the base panel mount 4 will taper inwardly (i.e., the thickness 34 of the base panel will decrease) as the base panel mount 4 extends upwardly. Also, a lower portion 38 of the thickness 34 of the base panel mount 4 will preferably taper inwardly (i.e., the thickness 34 of the base panel mount 4 will decrease) as the base panel mount 4 extends downwardly. The tapered upper portion 36 preferably begins at or in proximity to the closed lower ends 20 and 24 of the vertically extending left and right bracket slots 14 and 16 and preferably comprises the front 6 of the base panel mount 4 angling toward the back 8 of the base panel mount 4, and the back 8 of the base panel mount 4 angling toward the front 6 of the base panel mount 4, as the base panel mount 4 extends up tray The tapered lower portion 38 preferably begins at lower end of the tapered upper portion 36 and preferably comprises the front 6 of the base panel mount 4 angling toward the back 8 of the base panel mount 4, and the back 8 of the base panel mount 4 angling toward the front 6 of the base panel mount 4, as the base panel mount 4 extends downwardly.

Although the clipping base mount 2 and the left and right bracket slots 14 and 16 and/or other elements of the clipping base mount 2 are referred to above as extending vertically, upwardly, or downwardly, it will be understood that the clipping base mount 2 can be attached to a surface which is oriented vertically, horizontally, or at any angle between a horizontal and a vertical orientation.

An embodiment 40 of a perfusion instrument or equipment holder used in the inventive multipurpose holding apparatus for holding, a multi-stopcock manifold is, illustrated in FIGS. 6-11. A manufactured three stopcock manifold allows multiple infusions of mediations, drugs, or treatments to connect to a cardiac oxygenator's venous reservoir. Needle-free stopcocks and manifolds can significantly reduce the risk of contamination and bloodstream infection.

The manifold holder 40 comprises a holder body 42 having a clipping structure 44 which is provided on the body 42. The clipping structure 44 comprises an outwardly projecting left shoulder plate 46 and an outwardly projecting right shoulder plate 48 which is opposite and coplanar with the left shoulder plate 46. For removably attaching the manifold holder 40 to the clipping base mount 2, the left shoulder plate 46 of the manifold holder 40 slides downwardly into the vertically extending left bracket slot 14 of the clipping base 2 and the right shoulder plate 48 slides downwardly into the vertically extending right bracket slot 16. The thickness of the left and right shoulder plates 46 and 48 of the manifold holder 40 preferably matches the width 32 of the short clipping segments 30 in the bottoms of the left and right bracket slots 14 and 16 (i.e., the left and right shoulder plates 46 and 48 fit tightly in (or clip into) the clipping segments 30).

The body 42 of the manifold holder 40 comprises; a base 62 on which the multi-stopcock manifold will rest; an opening 50 for a horizontal tab of the multi-stopcock manifold; a stop or dead end 52 to hold the manifold in place; a pair of teeth 54 and 56 which project from the body 42 to slide into corresponding openings on the surface of the manifold structure to further secure the manifold in place; and a left side cover 60 which receives a corner or end portion of the manifold body to further hold the manifold in place.

An alternative embodiment 66 of a manifold holder which is used in inventive multipurpose holding apparatus to hold a multi-stopcock manifold is shown in FIGS. 12-17. The manifold holder 66 differs from the manifold holder 40 in that the angle of the clipping structure 68 of the manifold 66 is moved 90° with respect to the body 70 of the manifold holder 66. The manifold holder 66 also differs from the horizontal manifold holder 40 in that it can be placed on a horizontal curved base mount or a flat base mount 2 on a flat horizontal surface such as, e.g., a shelf.

An embodiment 72 of a perfusion instrument or equipment holder used in the inventive multipurpose holding apparatus for holding hemoconcentrator is illustrated in FIGS. 18-21. A hemoconcentrator is typically used to remove excess water from the patient's blood volume (known as ultrafiltration) during cardiovascular bypass surgery. The hemoconcentrator operates to reduce hemodilution and increase blood hematocrit levels, and reduce the need for giving packed red blood cells (PRBC).

The hemoconcentrator holder 72 comprises (a) a holder body 74 comprising a base wall 76 and (b) a clipping structure 78 which projects from the back side 80 of the base wall 76. The clipping structure 78 comprises an outwardly projecting left shoulder plate 82 and an outwardly projecting right shoulder plate 84 which is opposite and coplanar pith the left shoulder plate 82. For removably attaching the hemoconcentrator holder 72 to the clipping base mount 2, the left shoulder plate 82 slides downwardly into the vertically extending left bracket slot 14 of the clipping base mount 2 and the right shoulder plate 84 slides downwardly into the vertically extending right bracket slot 16. The thickness of the left and right shoulder plates 82 and 84 of the hemoconcentrator holder 72 preferably matches the width 32 of the short clipping segments 30 in the bottoms of the left and right bracket slots 14 and 16 (i.e., the left and right shoulder plates 82 and 84 fit tightly in (or clip into) the clipping segments 30).

The body 74 of the hemoconcentrator holder 72 further comprises: a longitudinal axis 86 (wherein the base wall 76 of the body 74 is preferably parallel to the longitudinal axis 86); a lower C-shaped clamping arm 88 which extends in a first direction from a first side 90 of the base wall 76; and an upper C-shaped clamping arm 92 which extends from a second side 94 of the base wall 76, opposite the first side 90, in a second direction which is opposite the first direction of the lower C-shaped clamping arm 88. A curve extending from a longitudinal centerline 96 of the base wall 76 to the outer end 98 of the lower C-shaped clamping arm 88 extends, more than 180° around the longitudinal axis 86. Similarly, a curve extending from the longitudinal centerline 96 of the base wall 76 to the outer end 100 of the upper C-shaped clamping arm 92 also extends more than 180° around the longitudinal axis 86.

The lower and upper C-shaped clamping arms 88 and 92 are preferably sized, and preferably have sufficient flexibility, for clamping around and holding a cylindrical portion of a hemoconcentrator. Examples of materials of construction having suitable flexibility and strength for clamping and holding a hemoconcentrator include, but are not limited to, Duraform plastic or PLA plastic.

The clipping structure 78 of the hemoconcentrator holder 72 preferably has a square shape so that (a) the hemoconcentrator holder 72 will hold the hemoconcentrator in a vertical orientation when the holder 72 is clipped into the clipping base mount 2 in the vertical orientation of the holder 72 shown in FIGS. 18-21 and (b) the hemoconcentrator holder 72 can be rotated 90° to hold the hemoconcentrator in a horizontal orientation wherein left and right shoulders 101 and 103 of the clipping structure 78 will be clipped into the clipping base mount 2.

An embodiment 102 of a perfusion instrument or equipment holder used in the inventive multipurpose holding apparatus wherein the body of the holder 102 is a tube clamp tray 104 is illustrated in FIGS. 22-24 and 33. The tube clamp tray 104 comprises: a longitudinal axis 105; a flat bottom surface 106 having a lower end 108 which is wider than the upper end 110 of the bottom surface 106; and a retaining wall 112 which extends upwardly from the periphery of the flat bottom surface 106. The upwardly extending retaining wall 112 surrounds the entire periphery of the flat bottom surface 106 of the tube clamp tray 104 except for the upper curl 110 of the bottom surface 104. In other words, the upwardly extending retaining wall 112 is open at the upper end of the tray 104.

The tube clamp holder 102 further comprises (a) a first clipping structure 114 which projects laterally outward, with respect to the longitudinal axis 105 of the tray 104, from one lateral side 116 of the upwardly extending retaining wall 112 and (b) an identical second clipping structure 118 which projects laterally outward, with respect to the longitudinal axis 105 of the tray 104, from the other lateral side 120 of the upwardly extending retaining wall 112. The first and second clipping structures 114 and 118 are oriented at an angle with respect to the clamp holding tray 104 such that, when either of the clipping structures 114 or 118 is received in the clipping base mount 2, the bottom surface 106 of the tray 104 will slope downwardly from the upper end 110 tip the lower end 108 of the tray 104 at an angle which is in a range of from 5° to 20°, more preferably from 5° to 15° or more preferably about 10° (i.e., 10°±10%), from horizontal.

The identical clipping structures 114 and 118 on opposite sides of the clamp holding tray 104 allow the tube clamp holder 102 to be selectively connected to the clipping base mount 2 such that the clamp holding tray 104 slopes downwardly to the left or to the right.

Each of the clipping structures 114 and 118 comprises a vertically extending, outwardly projecting left shoulder plate 124 and a vertically extending, outwardly projecting right shoulder plate 126 which is opposite and coplanar with the left shoulder plate 124. For removably attaching the tube clamp holder 102 to the clipping base mount 2, the left shoulder plate 124 of either clipping structure 114 or 118 slides downwardly into the vertically extending left bracket slot 14 of the clipping base mount 2 and the right shoulder plate 126 slides downwardly into the vertically extending right bracket slot 16. The thickness of the left and right shoulder plates 124 and 126 preferably matches the width 32 of the short clipping segments 30 in the bottoms of the left and right bracket slots 14 and 16 (i.e., the left and right shoulder plates 124 and 126 fit tightly in (or clip into) the clipping segments 30).

One or more, preferably a pair, of indentations 128 and 129 formed in the bottom of the tray 104 of the tube clamp holder 102 are provided for receiving one or more magnets 131, 133. The one or more magnets 131, 133 will preferably be glued into the one or more indentations 128 and 129 and will assist in holding the metal clamps in the clamp tray 104.

Figure 25:
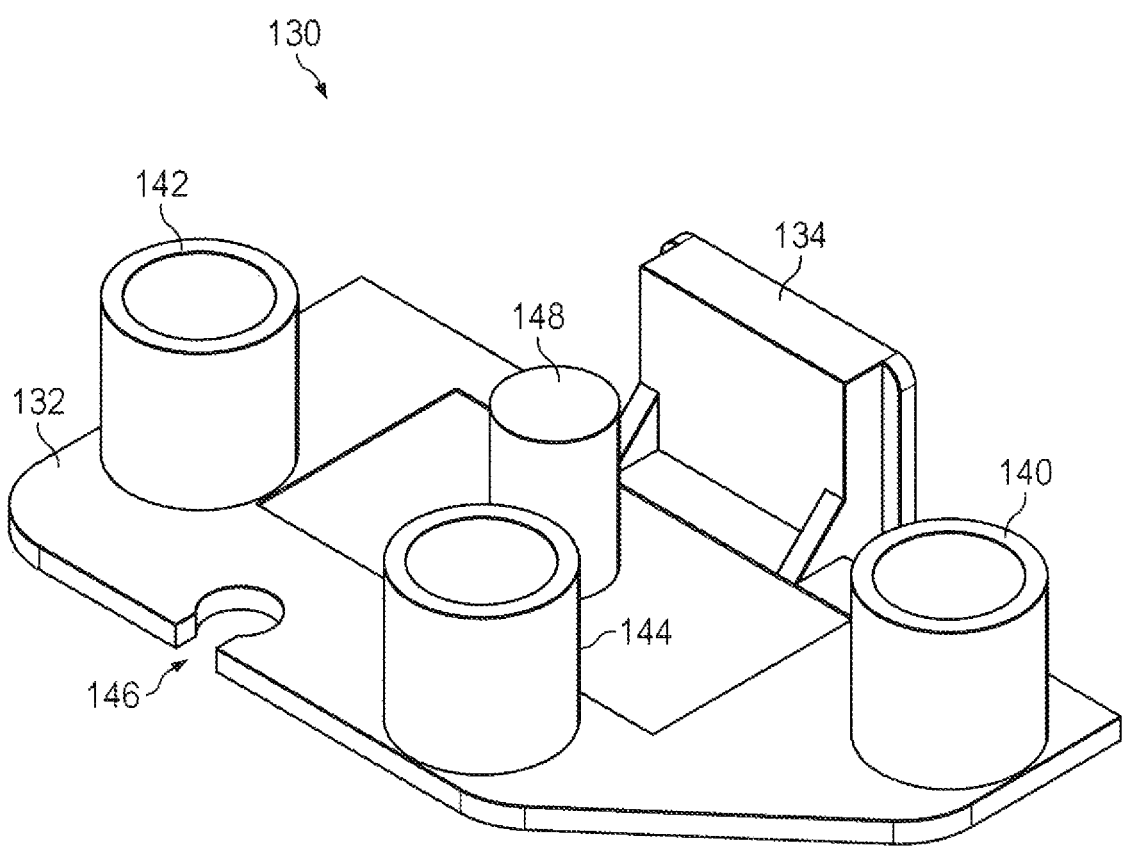
FIG. 25 is a perspective view of pan embodiment 130 of a perfusion instrument or equipment holder used in the inventive multipurpose holding apparatus for holding ultrasonic flow probes, temperature probes, and level detectors.
Figure 26:
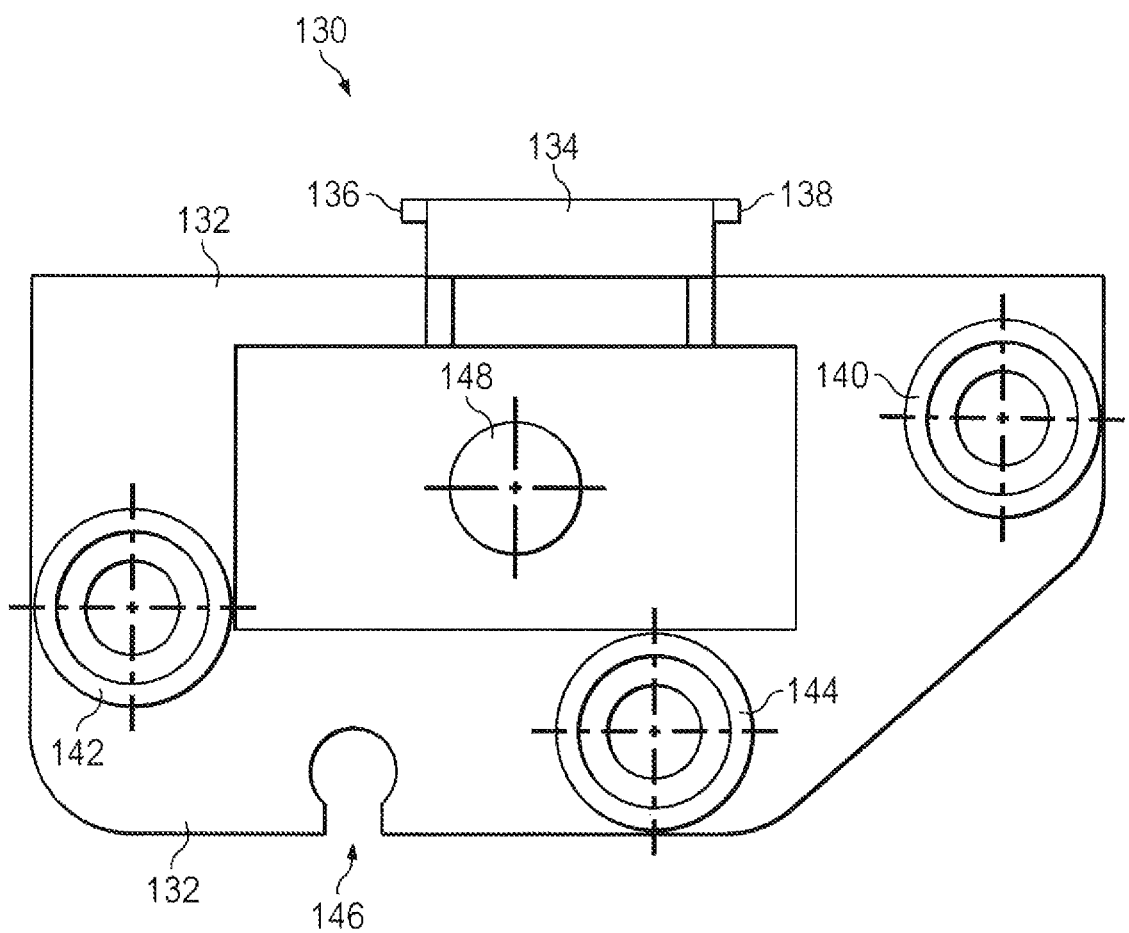
FIG. 26 is a top view of the holder 130.
Figure 27:
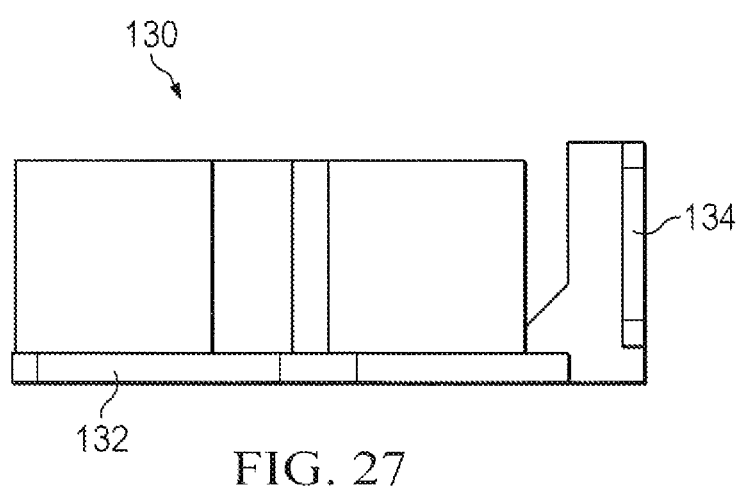
FIG. 27 is an elevational left side view of the holder 130.

An embodiment 130 of a perfusion instrument or equipment holder used in the inventive multipurpose holding apparatus for holding ultrasonic flow probes is illustrated in FIGS. 25-27. Ultrasonic flow probes are used in perfusion procedures to accurately measure the blood flow from the bypass machine to the patient.

The flow probe holder 130 comprises a holding tray or plate 132 and a clipping structure 134 which projects from an edge of, and is perpendicular to, the holding plate 132. The clipping structure 134 comprises a vertically extending, outwardly projecting left shoulder plate 136 and a vertically extending, outwardly projecting right shoulder plate 138 which is opposite and coplanar with the left shoulder plate 136. For removably attaching the flow probe holder 130 to the clipping base mount 2, the left shoulder plate 136 slides downwardly into the vertically extending left bracket slot 14 of the clipping base mount 2 and the right shoulder plate 138 slides downwardly into the vertically extending right bracket slot 16. The thickness of the left and right shoulder plates 136 and 138 of the flow probe holder 130 preferably hatches the width 32 of the short clipping segments 30 in the bottoms of the left and right bracket slots 14 and 16 (i.e., the left and right shoulder plates 136 and 138 fit tightly in (or clip into) the clipping segments 30).

The bolding tray or plate 132 of the flow probe holder 130 comprises one or more, preferably three, upwardly extending cups 140, 142, 144 which can receive and hold temperature probes and/or level sensors (e.g., TERUMO brand level sensors). Blood temperatures are measured during cardiovascular bypass. Level sensors are used to alert the perfusionist if the venous reservoir blood level drops to an unsafe level. A keyhole slot 146 is also preferably provided in the holding tray or plate 132 for retaining an alternative device or instrument such as a LIVA NOVA/SORIN brand level sensor. In addition, a post 148 preferably extends upwardly from the holding tray or plate 132 of the holder 130 for mounting the ultrasonic flow probe.

Figure 28:
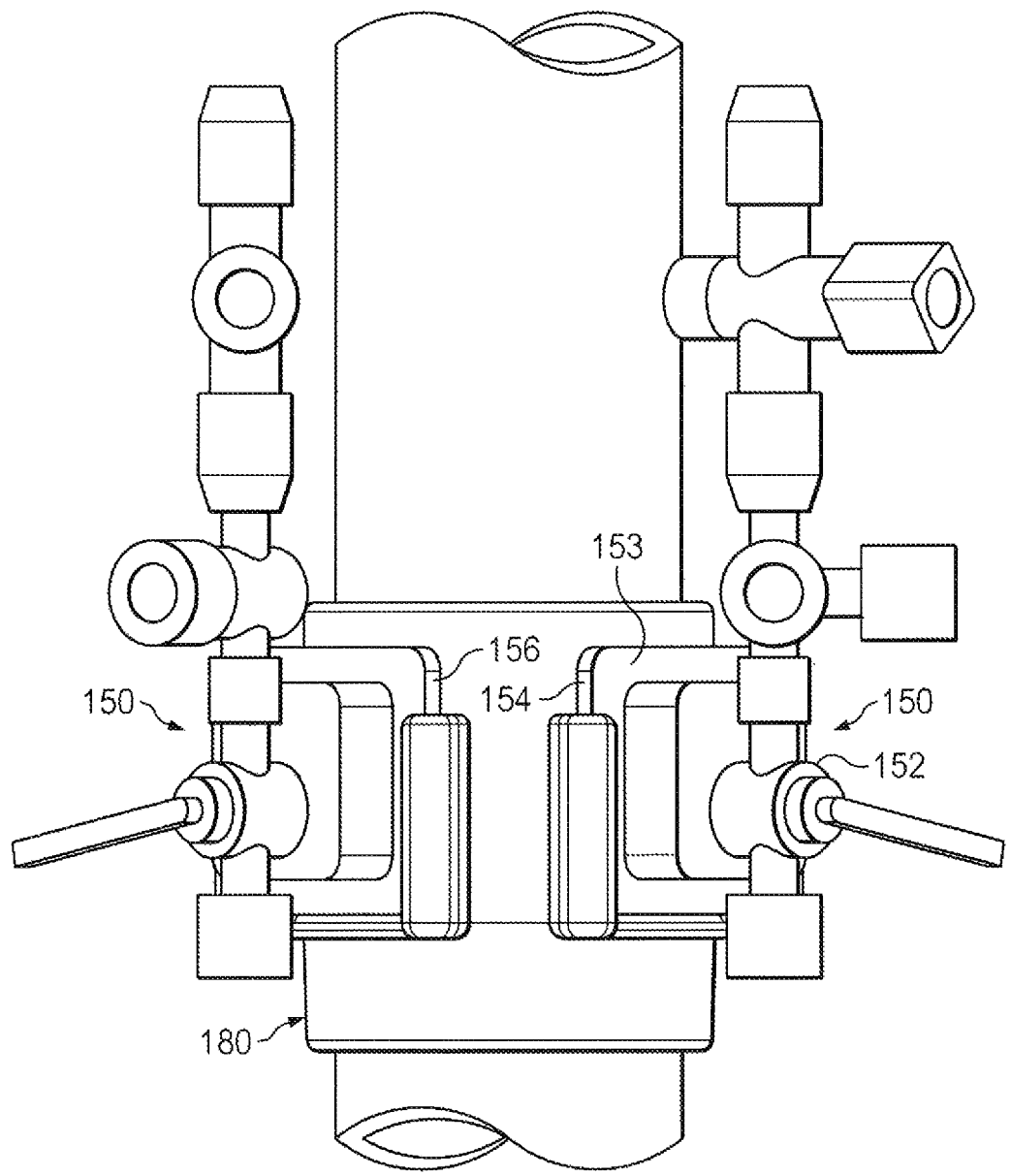
FIG. 28 depicts an embodiment 150 of the perfusion instrument or equipment holder used in inventive multipurpose holding apparatus for holding a pressure measurement transducer 152.

An embodiment 150 of the perfusion instrument or equipment holder used in inventive multipurpose holding apparatus for holding a pressure transducer 152 is illustrated in FIG. 28. Pressure transducers are used to monitor numerous pressures in a cardiovascular bypass circuit, e.g., pre and post oxygenator pressures, cardioplegia delivery pressure, and vacuum assist pressure.

The pressure transducer holder 150 includes a clipping structure 153 on the hack thereof which comprises an outwardly projecting left shoulder plate 154 and an outwardly projecting right shoulder plate 156 which is opposite and coplanar with the left shoulder plate 154. For removably attaching the transducer holder 150 to the clipping base mount 2, the left shoulder plate 154 slides downwardly into the vertically extending left bracket slot 14 of the clipping base mount 2 and the right shoulder plate 156 slides downwardly into the vertically extending right bracket slot 16. The thickness of the left and right shoulder plates 154 and 156 of the transducer holder 150 preferably matches the width 32 of the short clipping segments 30 in the bottoms of the left and right bracket slots 14 and 16 (i.e., the left and right shoulder plates 154 and 156 fit tightly in (or clip into) the clipping segments 30).

Figure 29:
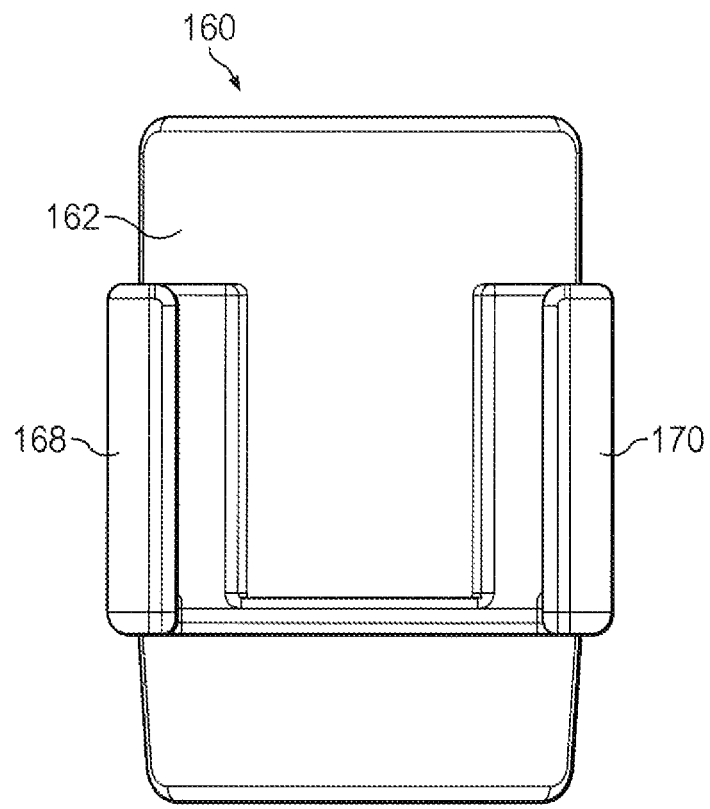
FIG. 29 is an elevational front view of an alternative curved embodiment 160 of the clipping base mount used in the inventive multipurpose holding apparatus.
Figure 30:
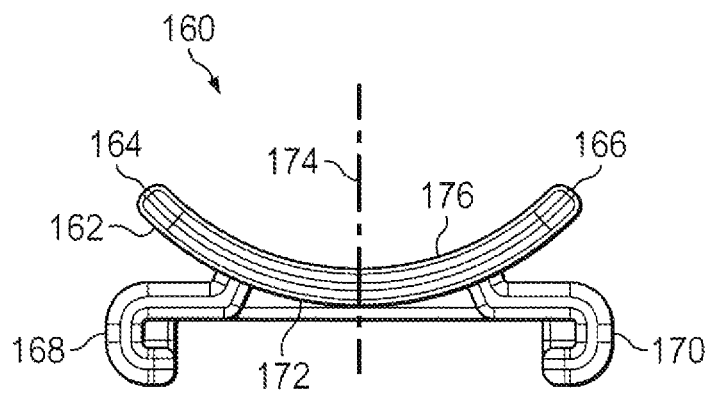
FIG. 30 is a top view of the alternative clipping base mount 160.

An alternative embodiment 160 of the clipping base mount used in the inventive multipurpose holding apparatus is illustrated in FIGS. 29 and 30. The clipping base mount 160 is substantially the same as the clipping base mount 2 described above except that (a) the base panel mount 162 of the clipping base mount 160 has a curved horizontal cross-sectional shape which curves from the left vertical edge 164 to the right vertical edge 166 of the base panel mount 162 for attaching the clipping base mount 160 to a curved surface and (b) the vertically extending, left and right clipping brackets 168 and 170 of the clipping base mount 160 extend outwardly a sufficient distance from the outwardly curved exterior 172 of the base panel mount 162 so that the curvature of the base panel mount 162 does not interfere with the attachment of any of the clipping structures 44, 68, 78, 114, 118, 134, or 152 of any of the instrument or equipment holders 40, 66, 72, 102, 130, or 150 described above to the clipping base mount 160.

The horizontal cross-sectional shape of the base panel mount 162 of the clipping base mount 160 is preferably semicircular. By way of example, but not by way of limitation, glue, other adhesives, or a hook and loop attachment can be used on the back surface 176 of the curved base panel mount 162 to attach the clipping base mount 160 to a curved surface (which can be vertical, horizontal, or any angle therebetween as noted above) in the perfusion treatment area. Alternatively, mechanical attachments (e.g., screws) could be used to attach the clipping base mount 160 to a curved surface where appropriate. Examples of typical structures and locations in perfusion treatment areas having curved surfaces to which the clipping base mount 160 can be attached include, but are not limited to support poles of bypass machines or intravenous poles.

Figure 31:
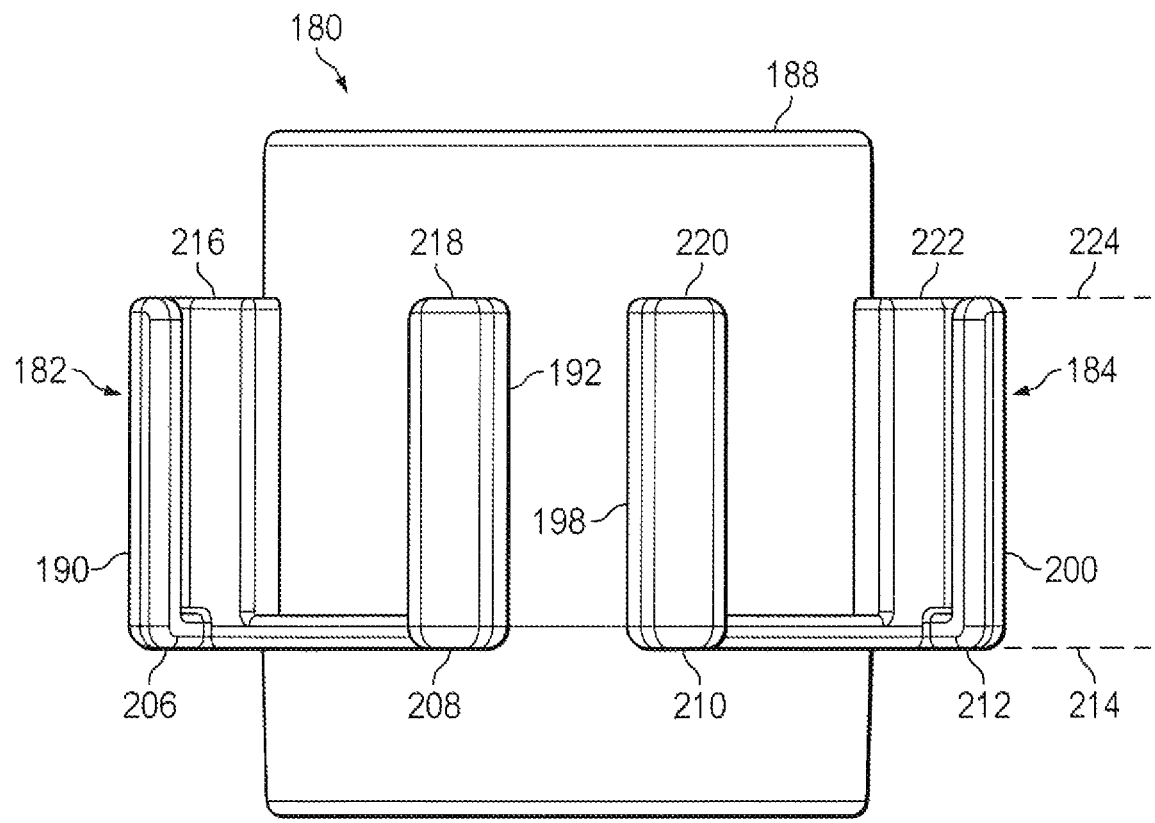
FIG. 31 is a front elevational view of an alternative curved embodiment 180 of the clipping base mount used in the inventive multipurpose holding apparatus.
Figure 32:
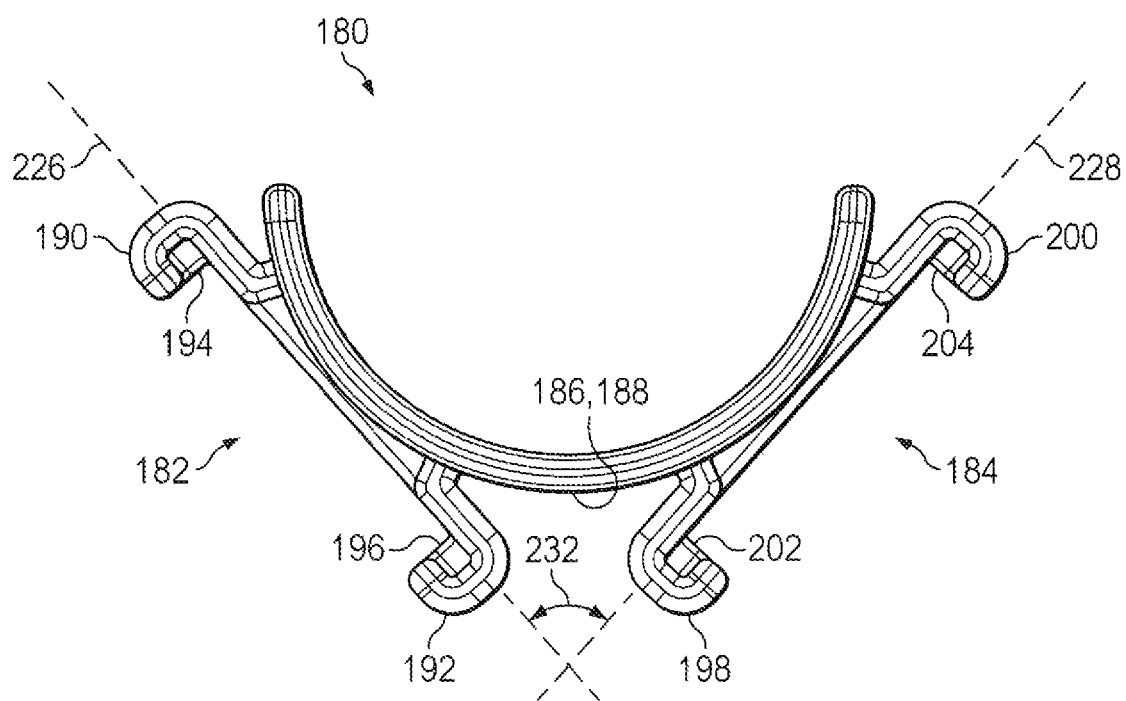
FIG. 32 is a top view of the curved alternative clipping base mount 180.
Figure 33:
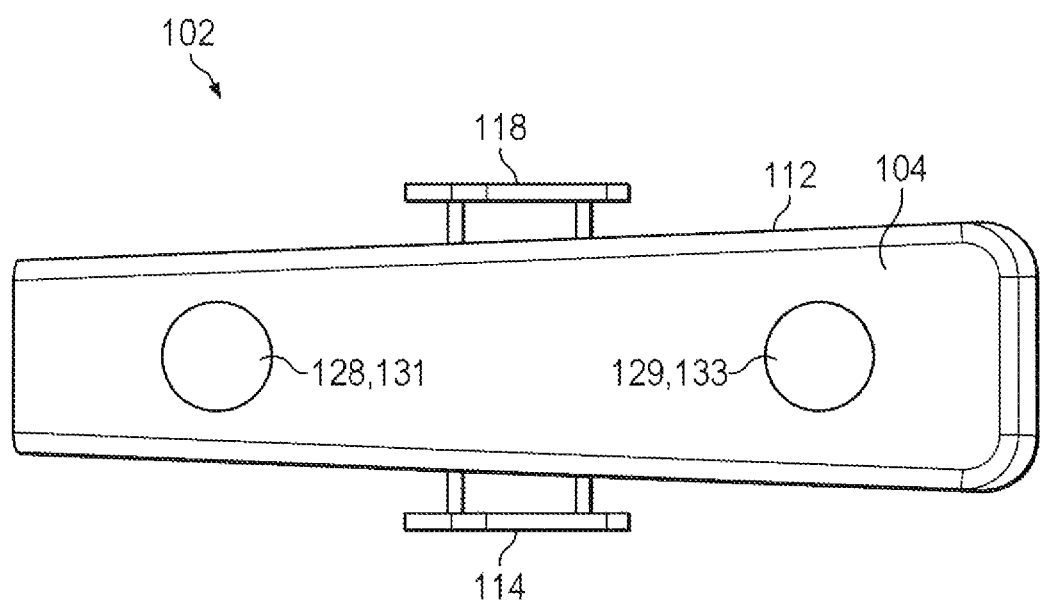
FIG. 33 is bottom view of the tube clamp tray holder 102.

Another curved embodiment 180 of the clipping base mount used in the inventive multipurpose holding apparatus is illustrated in FIGS. 31 and 32. The curved clipping base mount 180 is substantially the same as the curved clipping base mount 160 described above except that clipping base mount 180 has at least two pairs 182 and 184 of clipping brackets which project outwardly from the outwardly curved exterior surface 186 of the curved base panel mount 188. The first opposing pair 182 of vertically extending clipping backets 190 and 192 provides a vertically extending left bracket slot 194 which faces a vertically extending right bracket slot 196. The second opposing pair 184 of vertically extending clipping brackets 198 and 200 provides a vertically extending left bracket slot 202 which faces a vertically extending right bracket slot 204.

In the curved clipping base mount 180, each of the bottom cads 206, 208, 210, and 212 of the vertically extending clipping brackets 190 and 192 of the first pair 182 and the clipping brackets 198 and 200 of the second pair 184 is preferably located in the same lower horizontal plane 214. Each of the upper ends 216, 218, 220, and 222 of the vertically extending clipping brackets 190 and 192 of the first pair 182 and the clipping brackets 198 and 200 of the second pair 184 is preferably located in the same upper horizontal plane 224.

Each pair 182 and 184 of the clipping brackets of the curved clipping base 180 can hold a separate one of the instrument or equipment holders 40, 66, 72, 102, 130, or 150 describe above. The instrument or equipment holders received in the two pairs of clipping brackets 182 and 184 can be of the same type or can be different. As one example, one pressure transducer holder 150 could be held by the first pair of clipping brackets 182 and another pressure transducer holder 150 could be held by the second pair of clipping brackets 184. As another example, a pressure transducer holder 150 could be held by the first pair of clipping brackets 182 and a hemoconcentrator holder 72 could be held by the second pair of clipping brackets 184.

In each case, using a pair of pressure transducers 150 as an example, the two pairs of clipping brackets 182 and 184 of the curved clipping base 180 will preferably be spaced and oriented with respect to each other such that (a) the back surfaces of the left and right shoulder plates 154 and 156 of the pressure transducer 150 clipped into the first pair of clipping brackets 182 will lie in a first vertical plane 226, (b) the back surfaces of the left and right shoulder plates 154 and 156 of the pressure transducer 150 clipped into the second pair of clipping brackets 184 will lie in a second vertical plane 228, and (c) the second vertical plane 228 will intersect the first vertical plane 226, along a vertical line, at an angle 232 in the range of from 110° to 70°.

Thus, the present invention is well adapted to carry out the objects and attain the ends and advantages mentioned above as well as those inherent therein. While presently preferred embodiments been described for purposes of this disclosure, numerous changes and modifications will be apparent to those in the art. Such changes and modifications are encompassed within this in invention as defined by the claims.

What is claimed is:

1. An apparatus for perfusion procedures comprising:
a clipping base mount comprising a base panel mount having a front surface and an opposing pair of clipping brackets on an exterior of the front surface of the base panel mount, the opposing pair of clipping brackets comprising
a linear left bracket on the front surface of the base panel mount,
a linear right bracket on the front surface of the base panel mount which is spaced laterally apart from and parallel to the linear left bracket,
the linear left bracket comprising a linear left bracket slot within the linear left bracket which has an open upper end, a closed lower end, and a linear slot opening which extends from the open upper end to the closed lower end,
the linear right bracket comprising a linear right bracket slot within the linear right bracket which has an open upper end, a closed lower end, and a linear slot opening which extends from the open upper end of the linear right bracket slot to the closed lower end of the linear right bracket slot and is spaced laterally apart from and is parallel to the linear slot opening of the linear left bracket slot,
the linear slot opening of the linear left bracket slot facing the linear slot opening of the linear right bracket slot,
the linear left bracket slot, or at least a segment of the linear left bracket slot, having a width, between a flat rearward interior wall and a flat forward interior wall of the linear left bracket slot, which decreases as the linear left bracket slot extends downwardly to the closed lower end of the linear left bracket slot or to a clipping segment in a bottom end portion of the linear left bracket slot, and
the linear right bracket slot, or at least a segment of the linear right bracket slot, having a width, between a flat rearward interior wall and a flat forward interior wall of the linear right bracket slot, which decreases as the linear right bracket slot extends downwardly to the closed lower end of the linear right bracket slot or to a clipping segment in a bottom end portion of the linear right bracket slot and
a perfusion instrument or equipment holder comprising a holder body and a clipping structure, provided on the holder body, which is receivable in the opposing pair of clipping brackets,
the clipping structure of the perfusion instrument or equipment holder comprising a projecting left shoulder plate with a linear outer edge which slides into the linear left bracket slot and a projecting right shoulder plate with a linear outer edge which slides into the linear right bracket slot, the linear outer edge of the left shoulder plate being parallel to the linear outer edge of the right shoulder plate,
when the left shoulder plate and the linear outer edge thereof are received in the linear left bracket slot and the right shoulder plate and the linear outer edge thereof are received in the linear right bracket slot, the clipping structure and the holder body of the perfusion instrument or equipment holder are prevented from rotating with respect to the clipping base mount, and
the closed lower end of the linear left bracket slot preventing the linear outer edge of the left shoulder plate from extending through the closed lower end of the linear left bracket slot and the closed lower end of the linear right bracket slot preventing the linear outer edge of the right shoulder plate from extending through the closed lower end of the linear right bracket slot.

2. The apparatus of claim 1 further comprising:
The linear left bracket slot having the clipping segment in the bottom end portion of the linear left bracket slot;
the width of the linear left bracket slot being constant in the clipping segment in the bottom end portion of the linear left bracket slot as the clipping segment in the bottom end portion of the linear left bracket slot extends downwardly;
the linear right bracket slot having the clipping segment in the bottom end portion of the linear right bracket slot; and
the width of the linear right bracket slot being constant in the clipping segment in the bottom end portion of the linear right bracket slot as the clipping segment in the bottom end portion of the linear right bracket slot extends downwardly.

3. The apparatus of claim 1 further comprising:
the base panel mount having a back;
an upper portion of the front surface of the base panel mount angling toward the back of the base panel mount as the base panel mount extends upwardly; and
a lower portion of the front surface of the base panel mount angling toward the back of the base panel mount as the base panel mount extends downwardly.

4. The apparatus of claim 1 further comprising:
the base panel mount having a left edge and a right edge;
the base panel mount having a curved cross-sectional shape which curves from the left edge to the right edge; and
the opposing pair of clipping brackets projecting from an outwardly curved front surface of the base panel mount.

5. The apparatus of claim 4 further comprising the curved cross-sectional shape of the base panel mount being a semicircular cross-sectional shape.

6. The apparatus of claim 4 further comprising:
the opposing pair of clipping brackets being a first opposing pair of clipping brackets;
the clipping base mount further comprising a second opposing pair of clipping brackets which project outwardly from the outwardly curved front surface of the base panel mount, the second opposing pair of clipping brackets having a left bracket slot and a right bracket slot and the second opposing pair of clipping brackets being identical to the first opposing pair of clipping brackets;
the perfusion instrument or equipment holder being a first perfusion instrument or equipment holder; and
the apparatus further comprising a second perfusion instrument or equipment holder comprising a holder body and a clipping structure provided on the holder body of the second perfusion instrument or equipment holder, the clipping structure of the second perfusion instrument or equipment holder being receivable in the second opposing pair of clipping brackets, the clipping structure of the second perfusion instrument or equipment holder comprising a projecting left shoulder plate which slides into the left bracket slot of the second opposing pair of clipping brackets and a projecting right shoulder plate which slides into the right bracket slot of the second opposing pair of clipping brackets.

7. The apparatus of claim 6 further comprising:
the curved cross-sectional shape of the base panel being a semicircular cross-sectional shape and
each of the left and right brackets of each of the first and the second opposing pairs of clipping brackets having a bottom end which lies in a first plane and a top end which lies in a second plane which is parallel to the first plane.

8. The apparatus of claim 7 further comprising:
the left shoulder plate of the clipping structure of the first perfusion instrument or equipment holder having a back surface which lies in a first orientational plane;
the right shoulder plate of the clipping structure of the first perfusion instrument or equipment holder having a back surface which also lies in the first orientational plane;
the left shoulder plate of the clipping structure of the second perfusion instrument or equipment holder having a back surface which lies in a second orientational plane;
the right shoulder plate of the clipping structure of the second perfusion instrument or equipment holder having a back surface which also lies in the second orientational plane; and
when the clipping structure of the first perfusion instrument or equipment holder is received in the first opposing pair of clipping brackets and the clipping structure of the second perfusion instrument or equipment holder is receive in the second opposing pair of clipping brackets, the second orientational plane intersects the first orientational plane at an angle in a range of from 110° to 70°.

9. The apparatus of claim 1 further comprising the perfusion instrument or equipment holder being a manifold holder for a stopcock manifold.

10. The apparatus of claim 1 further comprising the perfusion instrument or equipment holder being a hemoconcentrator holder.

11. The apparatus of claim 1 further comprising the perfusion instrument or equipment holder being a pressure transducer holder.

12. The apparatus of claim 1 further comprising the perfusion instrument or equipment holder being a tube clamp tray holder.

13. The apparatus of claim 1 further comprising the perfusion instrument or equipment holder being an ultrasonic flow probe holder.

14. The apparatus of claim 1 further comprising the clipping structure having a square shape.

* * * * *